United States Patent [19]
Kelderman

[11] Patent Number: 5,918,452
[45] Date of Patent: Jul. 6, 1999

[54] FOLDABLE, PULL-TYPE, V-RAKE APPARATUS

[76] Inventor: Gary L. Kelderman, 2674 Highway 92, Oskaloosa, Iowa 52577

[21] Appl. No.: 08/904,793

[22] Filed: Aug. 1, 1997

[51] Int. Cl.$^6$ .................................................. A01D 78/00
[52] U.S. Cl. ............................................... 56/377; 56/380
[58] Field of Search .......................... 56/375, 377, 378, 56/380, 379, 384, DIG. 21, 365, 367, 372, 370

[56] References Cited

U.S. PATENT DOCUMENTS

| | | |
|---|---|---|
| 2,925,700 | 2/1960 | Plant . |
| 3,031,834 | 5/1962 | Van Der Lely et al. .................. 56/377 |
| 4,047,370 | 9/1977 | Eve . |
| 4,183,198 | 1/1980 | Sligter . |
| 4,446,685 | 5/1984 | Coeffic ...................................... 56/377 |
| 4,920,735 | 5/1990 | Bailey et al. . |
| 4,932,197 | 6/1990 | Allen ........................................ 56/377 |
| 4,947,631 | 8/1990 | Kuehn . |
| 5,062,260 | 11/1991 | Tonutti ..................................... 56/377 |
| 5,155,986 | 10/1992 | Kelderman . |
| 5,199,252 | 4/1993 | Peeters ..................................... 56/377 |
| 5,305,590 | 4/1994 | Peeters ..................................... 56/377 |
| 5,540,040 | 7/1996 | Peeters ..................................... 56/377 |
| 5,598,691 | 2/1997 | Peeters ..................................... 56/377 |
| 5,685,135 | 11/1997 | Menichetti ................................ 56/365 |

FOREIGN PATENT DOCUMENTS

| | | |
|---|---|---|
| 3418352A1 | 5/1984 | Germany . |
| 957524 | 5/1964 | United Kingdom ..................... 56/377 |

OTHER PUBLICATIONS

ICAM s.r.l.; "Mounted Side–Delivery Rake" Series IR/3 —IR/4 —IR/5 —IRV/8 —IRV/10; consisting of four (4) pages. Non dated.

Kelderman Rake Caddy Brochure; Kelderman Manufacturing, Inc. consisting of one sheet. No date.

Kelderman Manufacturing, Inc.; "Kelderman K–7 & K–9 Pull–Type Wheel Rakes" brochure consisting of one sheet with print on both front and back. No date.

2–pages (Copy) from Tri–State Neighbor publication dated Apr. 11, 1997 shows GEHL Hydra–Fold V–Rakes, No date.

1 page (COPY) from Tri–State Neighbor publication, dated Apr. 11, 1997 shows a ROWSE V–Rake as shown by post–it note —p. 10C.

1 page (COPY) from Tri–State Neighbor publication, dated Apr. 11, 1997, p. 11C shows VERMEER V–Rake —as shown by post–it note.

*Primary Examiner*—Terry Lee Melius
*Assistant Examiner*—Arpad Fabian Kovacs
*Attorney, Agent, or Firm*—Henderson & Sturm

[57] ABSTRACT

A pull-type V-rake apparatus for use in raking cut vegetation. The V-rake is comprised of a left hand, side discharge, wheel rake assembly and a right hand, side discharge, wheel rake assembly operably connected by a forward pivotal subframe and a rearward pivotal subframe for use as a single implement. The left and right hand rake assemblies are hydraulically actuated to fold from an operative field position to a transport position. The transport profile being narrow enough to be pulled behind the farm vehicle down a roadway. When the V-rake is in its operative field position, the left and right wheel rake assemblies form a "V". The cut vegetation is raked inwardly and rearwardly on the right side and the left side discharging the cut vegetation in the middle at the apparent vertex of the rakes to produce a single larger windrow as the V-rake traverses the field. The wheel rakes on the wheel rake assemblies are vertically adjustable from a transport position to an operative field position and are spring biased thereby enabling each wheel rake to articulate along a vertical arc when encountering an obstruction. The rake assemblies are able to articulate front-to-rear and side-to-side allowing the wheel rakes to maintain substantial contact with the cut vegetation at all times to ensure that no cut vegetation will be skipped as the V-rake traverses uneven terrain.

22 Claims, 5 Drawing Sheets

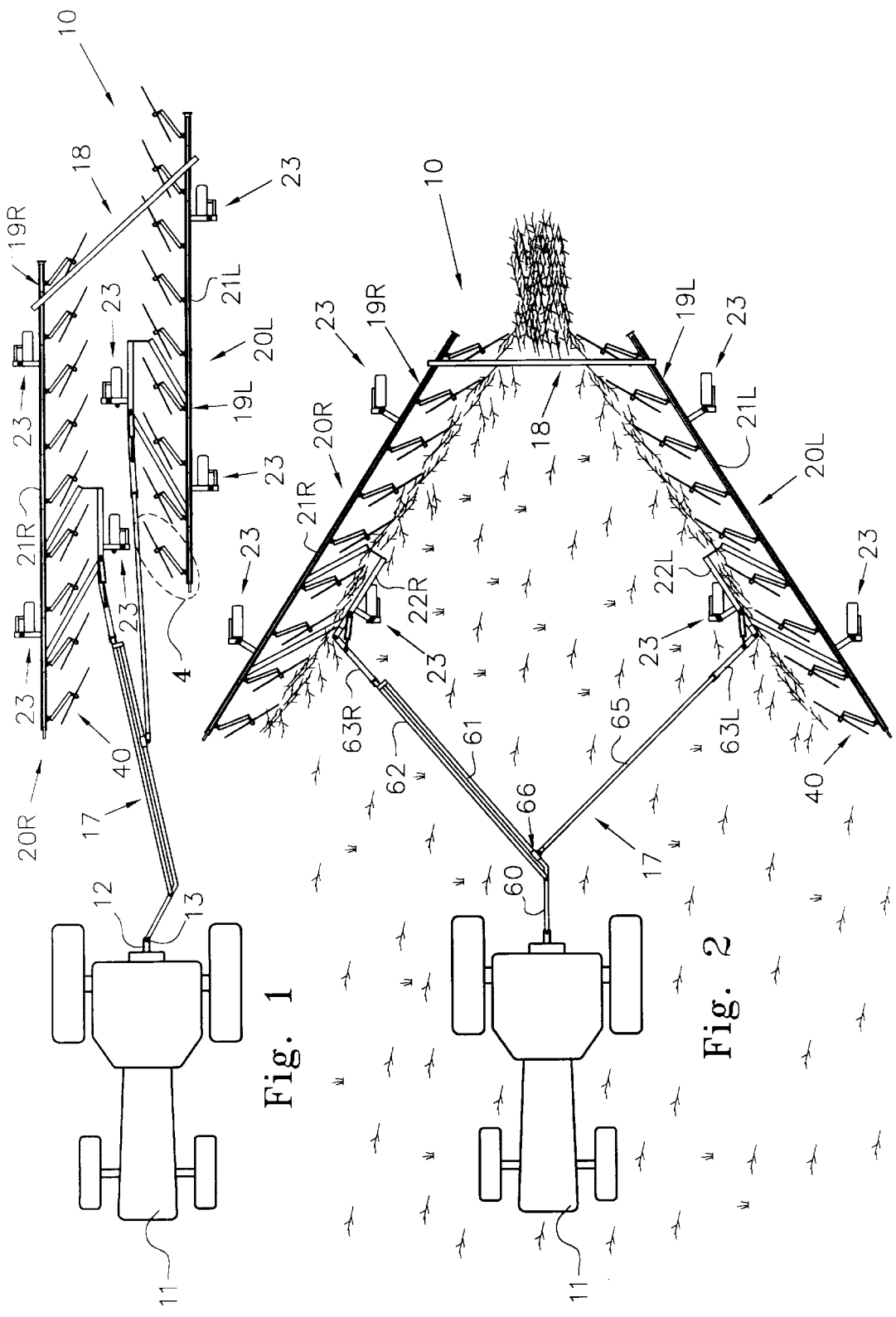

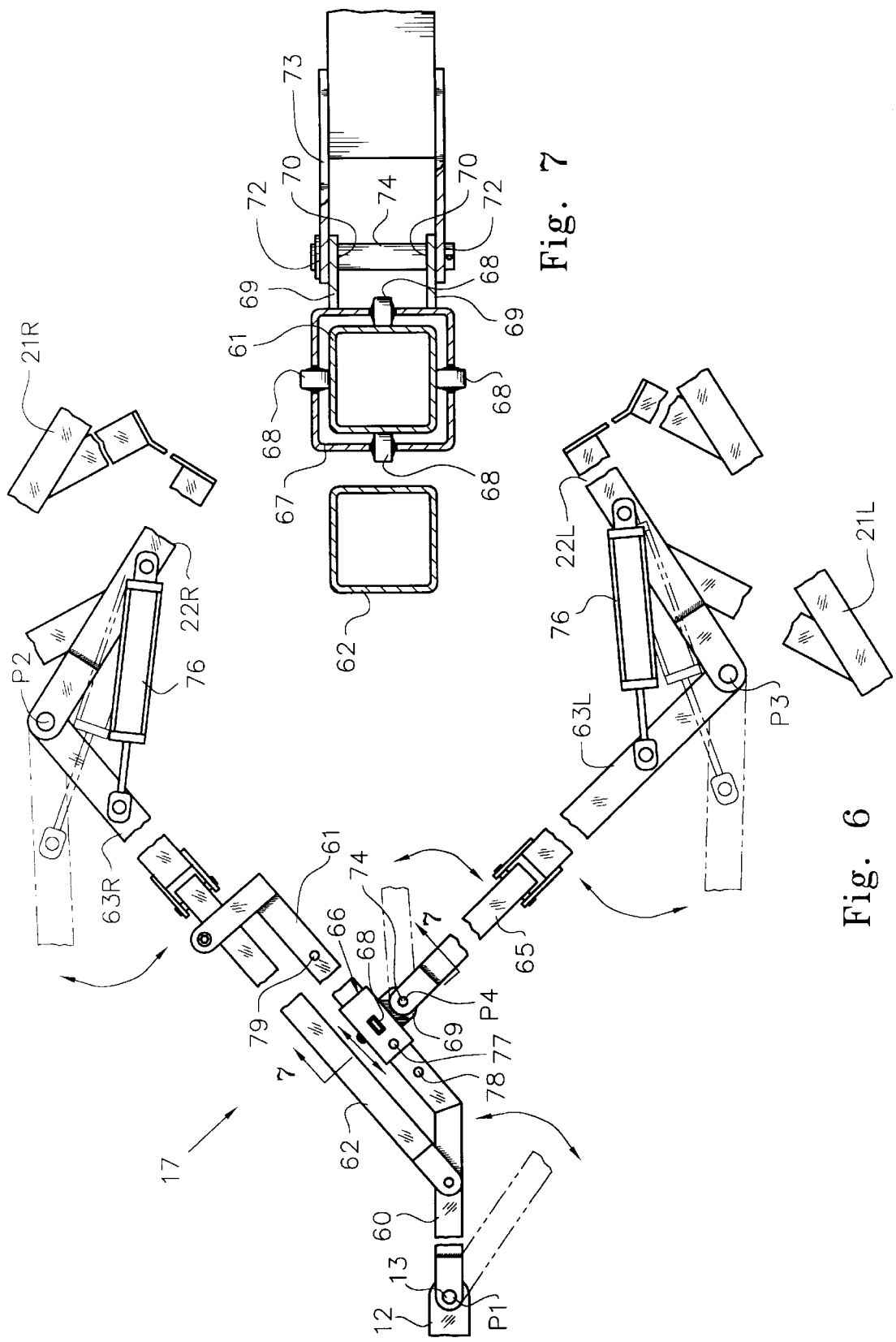

FOLDABLE, PULL-TYPE, V-RAKE APPARATUS

CROSS-REFERENCE TO RELATED APPLICATIONS

Not applicable.

STATEMENT REGARDING FEDERALLY SPONSORED RESEARCH OR DEVELOPMENT

Not applicable.

MICROFICHE APPENDIX

Not applicable.

BACKGROUND OF THE INVENTION

1. Field of the Invention

This invention relates generally to side delivery, pull-type, wheel rake implements, and more particularly to a pull-type V-rake apparatus constructed by operatively connecting a right hand, side delivery, pull-type, wheel rake and a left hand, side delivery, pull-type, wheel rake.

2. Description of Prior Art

Side delivery, pull-type rake implements have been in use for a number of years for raking cut vegetation, such as hay or straw, into windrow so that a baler, stacker or the like, can pick up the windrow to form bales, stacks or the like. One of the most common types of side delivery rakes is commonly referred to as a wheel rake. A typical wheel rake has a plurality of wheels with evenly spaced tines extending radially outwardly therearound. These tined wheels are freely rotatable about a central axis and are disposed in an overlapping relationship with the adjacent tined wheels such that each tined wheel is disposed forwardly and to one side of the following adjacent wheel. The rake implement is disposed diagonally rearwardly to the forward direction of movement of the implement, such that as the rake implement is pulled forwardly by a prime mover, the tines of the tined wheels brush against the cut stalks or surface of the earth causing the tined wheels to rotate about their central axis. The cut vegetation lying on top of the cut stalks or surface of the earth is picked up by the rotating tines and thrown rearwardly to the following adjacent tined wheel until the cut vegetation is discharged by the last tined wheel, resulting a windrow of cut vegetation.

Farmers and ranchers in the upper Midwest and western United States, having large fields, use these side discharge, pull-type wheel rake implements extensively, and have increasing sought larger rakes to reduce the number of passes, time, and fuel needed to rake the cut vegetation into windrows. Additionally, farmers and ranchers wishing to bale hay or straw that is relatively light, also desire larger rakes in order to create windrows of sufficient size in the fewest number of passes to make baling the vegetation more cost effective.

Unfortunately, there is a practical size limit to these pull-type rakes. The rakes can only be made so long while still being able to be transported from field to field down roadways behind a tractor or other farm vehicle. Therefore, there is a need for a pull-type rake implement that can meet the needs of farmers and ranchers desiring larger rakes while at the same time being easy to transported from field to field.

V-rakes, such as that disclosed in U.S. Pat. No. 4,947,631 issued to Kuehn have been designed to overcome some of these problems. The Kuehn V-rake is comprised of a left hand rake and a right hand rake operably connected such that the right side and the left side discharge the hay inwardly and rearwardly in the middle at the apparent vertex of the rakes to produce a single larger windrow as the V-rake traverses the field. The advantage of the V-rake is that it can cover a larger area than a single rake but yet is foldable for transport down a roadway. The Kuehn V-rake or the V-rake disclosed in U.S. Pat. No. 4,932,197 issued to Allen incorporate a central transport frame to which is pivotally attached the left and right rake assemblies. This central transporting frame has a limiting effect on the size of the rake assemblies that it can support. Additionally, the use of a central transporting frame does not allow the individual rake assemblies to articulate independently when traversing uneven terrain resulting in the wheel rakes skipping over the cut vegetation. This inability of the rake assemblies to articulate independently is a major disadvantage of the prior art particularly as the length or size of the rake increases. For example, when each rake assembly is fixed to a central transport frame, the terrain under the rake assemblies in their operative field position may be higher or lower than the terrain under the central transport frame. If the terrain is lower under the extended rake assembly than the terrain under the central transport frame the rakes will skip over the cut vegetation.

Consequently, there is a need for a pull-type wheel rake apparatus which takes advantage of the more economical V-type rake and yet overcomes the current problems associated with the V-type rake with regard to size limitations, the inability of the extended rake assemblies to articulate independently of each other when traversing uneven terrain and the inability to fold to a narrow enough profile for easy transport behind a vehicle down a roadway.

BRIEF SUMMARY OF THE INVENTION

The present invention relates to a pull-type V-rake comprised of a common right hand wheel rake assembly and a mirror image left hand wheel rake assembly operably connected for use as a single implement. The left and right hand rake assemblies are pivotally connected and hydraulically actuated to fold for ease of transport behind a tractor or other farm vehicle. The transport profile being narrow enough to be pulled behind the farm vehicle down a roadway. The rake can be unfolded to an operative field position wherein the left and right wheel rake assemblies form a "V". This V-type rake rakes the hay inwardly and rearwardly on the right side and the left side discharging the hay in the middle at the apparent vertex of the rakes to produce a single larger windrow as the V-rake travels through the field. The individual rake assemblies are also able to articulate independently of each other in their operative field position as the rake traverses uneven terrain.

BRIEF DESCRIPTION OF THE SEVERAL VIEWS OF THE DRAWINGS

FIG. 1 shows a plan view of the pull-type, V-rake apparatus of the present invention in the folded, transport position being pulled behind a tractor;

FIG. 2 shows a plan view of the pull-type, V-rake apparatus of the present invention in an operative field position being pulled behind a tractor;

FIG. 6 is an enlarged partial plan view of the forward pivotal subframe;

FIG. 7 shows a cross-sectional view of the roller assembly taken along lines 7—7 of FIG. 6;

DETAILED DESCRIPTION OF THE INVENTION

Figure 3:
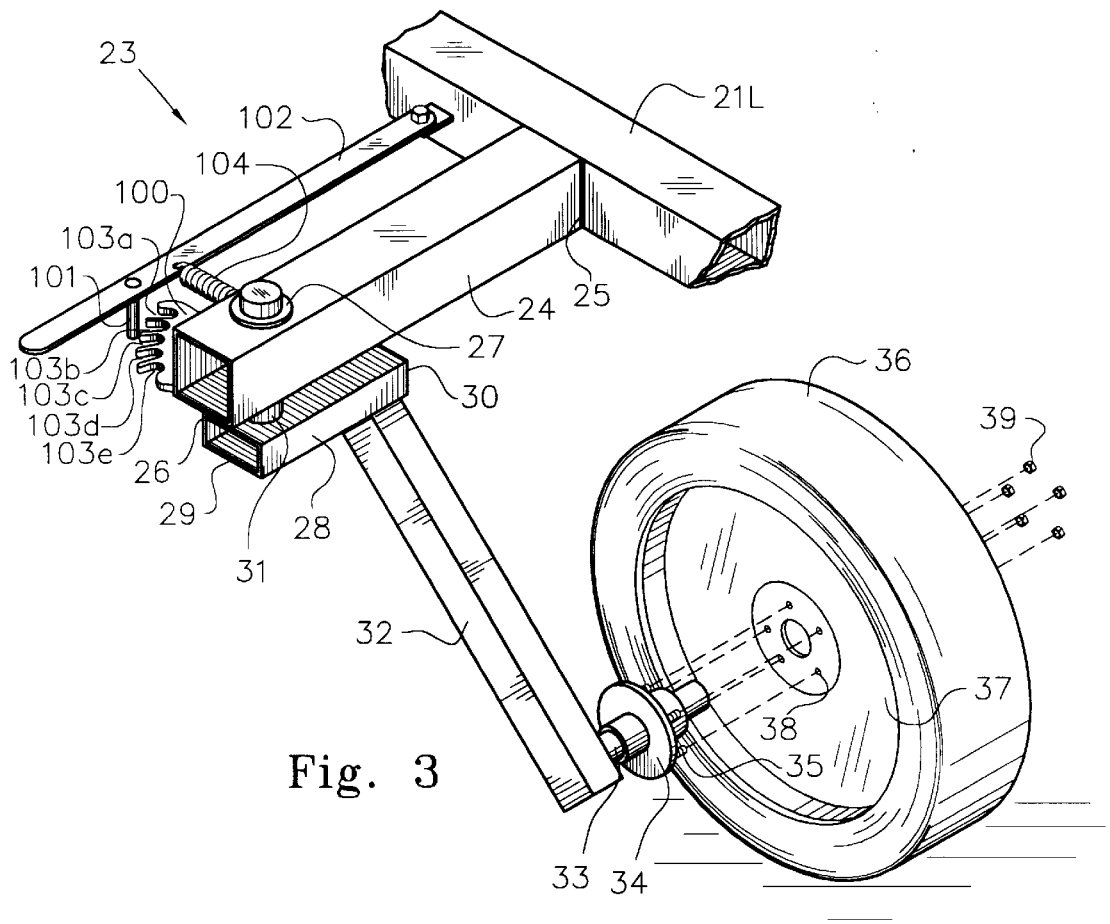
FIG. 3 shows a perspective view of a typical pivoting wheel assembly with a wheel locking device attached thereto.

Referring now to the drawings wherein like reference numerals designate identical or corresponding parts throughout the several views, FIG. I shows a plan view of the pull-type V-rake apparatus (10) of the present invention folded in the transport position. FIG. 2 shows a plan view of the pull-type V-rake implement (10) of the present invention in the operative field position. The V-rake (10) is shown being pulled by a prime mover (11), typically a tractor. The V-rake (10) is connected to the prime mover's draw bar (12) by a draw bar pin (13) (see FIG. 6 for an enlarged view).

The V-rake (10) is comprised of a common right hand rake assembly (20R) and a mirror image left hand rake assembly (20L) both pivotally attached at their forward ends and rearward ends by a forward pivotal subframe (17) and a rearward pivotal subframe (18) respectively. It should be understood that any reference to a "forward" end refers to an end disposed toward the forward direction of travel and any reference to a "rearward" end refers to an end disposed away from the forward direction of travel.

Each wheel rake assembly (20R and 20L) is comprised of a frame (19R and 19L) having a main horizontal beam (21R and 21L) and an inwardly disposed intermediate subframe (22R and 22L) rigidly attached thereto. The frame (19R or 19L) is supported by three pivotal castor wheel assemblies (23). A perspective view of a typical pivotal castor wheel assembly (23) is shown in FIG. 3. Wheel support beams (24), having a first end (25) and a second end (26), are rigidly fixed at their first ends (25) perpendicular to the main horizontal beam (21R or 21L). Near the second end (26) of the wheel support beams (24) is secured a vertical castor bearing (27). Positioned below the wheel support beam (24) is a horizontally disposed arm (28) having a first end (29) and a second end (30). Near the first end (29) of the horizontally disposed arm (28) is rigidly attached a vertical shaft (31) which is received by the vertical castor bearing (27). Fixed to the second end (30) of the horizontally disposed arm (28) is a diagonally disposed downward projecting arm (32). The diagonally disposed arm (32) terminates with a horizontal, perpendicular shaft (33). Fixed to this shaft (33) is a sealed wheel bearing hub (34). The wheel bearing hub (34) is rotatable about the shaft (33) and includes a plurality of lugs (35) disposed radially about the horizontal axis of the shaft (33). A wheel (36) having an annular rim (37) with a plurality of matching apertures (38) is aligned with the lugs (35) of the wheel bearing hub (34). The wheel (36) is securely attached to the hub (34) with lug nuts (39) thereby allowing the wheel (36) to rotate with the hub (34) about the horizontal axis of the shaft (33). The castor wheel assembly (23) is also free to pivot about the vertical axis of the vertical shaft (31) projecting through the vertical castor bearing (27) at the second end (26) of the wheel support beam (24).

On at least one of the rearward pivotal castor wheel assemblies (23) is a wheel locking bracket (100) which is rigidly fixed to the horizontally disposed arm (28). The wheel locking bracket (100) acts to lock the pivotal castor wheel assembly (23) at predetermined angles so that the wheel (36) will be parallel with the forward direction of travel. For example, to lock the castor wheel assembly (23) into the transport position, the wheel (36) and horizontally disposed arm (28) must be rotated until the pin (101) fixed to the lever (102) engages the first notch (103a) of the wheel locking bracket (100). A spring (104) acts as a bias to keep the pin (101) within the notch of the wheel locking bracket (100). If it is desired to lock the wheel assembly (23) so that the wheel rake assemblies (20R and 20L) are extended to the widest possible operative field position, the wheel (36) and horizontally disposed arm (28) must be rotated until the pin (101) engages the last notch (103e) of the wheel locking bracket (100). Additional notches (103b, 103c and 103d) are included so that the wheel rake assemblies (20R and 20L) may be set at intermediate positions between the narrowest possible transport position and widest possible operative field position. Typically the notches are set at equally spaced intervals such that the wheel rake assemblies (20R and 20L) can be extended outwardly every ten degrees, thereby creating a 10, 20, 30, or 40 degree "V".

Figures 4, 5:
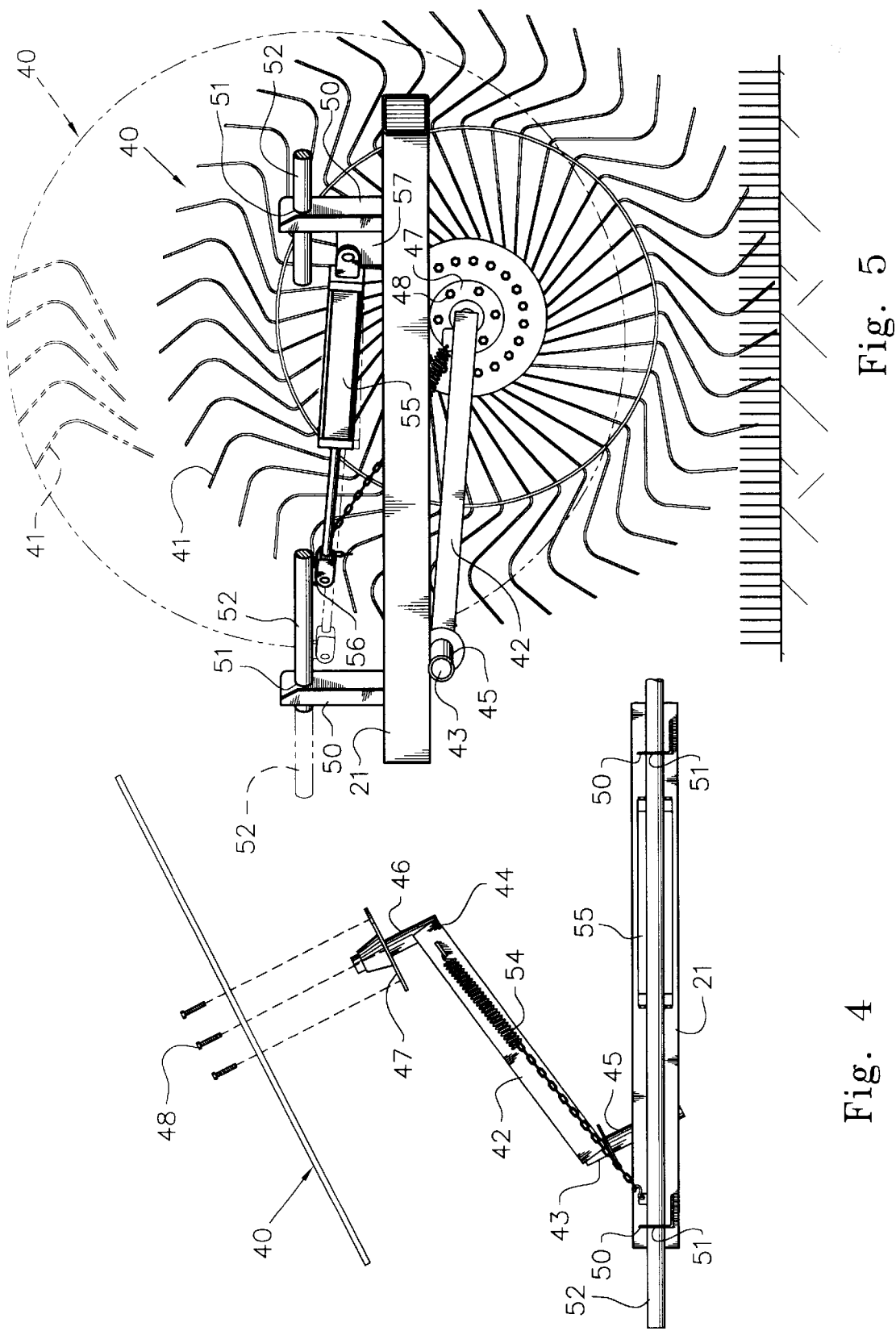
FIG. 4 shows an enlarged exploded plan view of a single wheel rake from FIG. 1.
FIG. 5 is a side elevation view of the wheel rake as viewed along lines 5—5 of FIG. 4 and illustrates the ability of the wheel rake to be moved from a transport position to an operative field position.

Each wheel rake assembly (20R and 20L) is further comprised of a plurality of equally spaced wheel rakes (40). As shown in FIGS. 1 and 2, each wheel rake (40) is positioned in an overlapping relationship with the adjacent wheel rake (40) such that each wheel rake (40) is disposed forwardly and to one side of the following adjacent wheel (40). FIG. 4 shows an enlarged exploded plan view of the singular wheel rake (40) shown in FIG. 1. FIG. 5 is a rear view of the wheel rake (40) as viewed along lines 5—5 of FIG. 4. Each wheel rake (40) is comprised of a plurality of radially disposed outward projecting tines (41). A wheel rake support arm (42) is rotatably attached at its first end (43) to the horizontal main beam (21R or 21L) by a sleeve (45). The second end (44) of the wheel rake support arm (42) terminates with a shaft (46) to which is fixed a rotatable, sealed, wheel rake hub bearing (47). A plurality of apertures radially disposed around the axis of the hub (47) receive threaded connectors (48) which secures the wheel rake (40) to the rotatable hub (47) and wheel rake support arm (42). The wheel rake is therefore free to rotate about the longitudinal axis of the hub (47) and the shaft (46).

Further comprising the wheel rake assemblies (20R and 20L) are a plurality of equally spaced vertically disposed rod brackets (50) projecting upwardly from the top face of the main horizontal beams (21). Each vertical rod bracket (50) includes an aperture (51) for receiving a movable rod (52) disposed above the length of the main horizontal beam (21). Positioned between the first two vertical rod brackets (50) is a hydraulic cylinder (55). One end of the cylinder (55) is pivotally connected to the rod (52) by a first cylinder bracket (56) and the other end of the cylinder (55) is pivotally connected to the main horizontal beam (21R or 21L) by a second cylinder bracket (57).

The wheel rake (40) is movable from a transport position, shown in phantom lines in FIG. 5, to an operative field position, shown in solid lines in FIG. 5, in the following manner. As the piston of the hydraulic cylinder (55) is withdrawn, the rod (52) is forced rearwardly, sliding within the apertures (51) in the rod brackets (50). As the rod (52) moves rearwardly, a chain and spring linkage (54), connected at one end to the rod (52) and connected at the other end to the wheel rake support arm (42), also moves rearwardly, thus allowing the wheel rake support arm (42) to rotate in a vertical arc downwardly about the horizontal axis of the shaft (46) within the sleeve (45). Further, this pivoting ability of the wheel rake support arm (42), in conjunction with the bias of the springs in the chain and spring linkage (54), enables the wheel rake support arms (42) to articulate vertically when the wheel rake (40) encounters an obstruction, such as a rock, thus enabling the wheel rakes (40) to bounce and float independently over obstructions in the terrain.

Referring now to FIG. 6, an enlarged partial plan view of the forward pivotal subframe (17) is shown. The forward pivotal subframe (17) is comprised of a tow bar (60) which is connected to the prime mover's draw bar (12) by a draw bar pin (13). It should be understood that the tow bar (60) is free to pivot laterally about the draw bar pin (13) and draw bar (12) such as when the prime mover (11) turns or when the V-rake (10) is being folded or unfolded.

Fixed to the rearward end of the tow bar (60) is a slide bar (61) extending obliquely rearwardly. Parallel to the slide bar (61) is a first connecting beam (62). The forward end of the first connecting beam (62) is pivotally attached to the rearward end of the tow bar (60). The slide bar (61) and the first connecting beam (62) are rigidly fixed near their rearward ends. The rearward end of the first connecting beam (62) is pivotally attached to the forward end of a second connecting beam (63R). The rearward end of the second connecting beam (63R) is pivotally connected to the right intermediate subframe (22R) which is in turn rigidly fixed to the main horizontal beam (21R) of the right handed wheel rake assembly (20R). A third connecting beam (65) is pivotally connected at its forward end to a roller assembly (66) which is free to slide along the length of the slide bar (61) as seen when comparing FIGS. 1 and 2. The rearward end of the third connecting beam (65) is pivotally connected to the forward end of the fourth connecting beam (63L). The rearward end of the fourth connecting beam (63L) is pivotally connected to the left intermediate subframe (22L) which is in turn connected to the main horizontal beam (21L) of the left handed wheel rake assembly (20L). Pivotally mounted to the top face of the second and fourth connecting beams (63R and 63L) and top face of the intermediate subframe (22R and 22L) are hydraulic cylinders (76). It should be understood that the second and fourth connecting beams (63R and 63L) are identical elements and the intermediate subframes (22R and 22L) and main horizontal beams (21R and 21L) are mirror images of each other.

FIG. 7 shows a cross-sectional view of the roller assembly (66) taken along lines 7—7 of FIG. 6. A rectangular sleeve (67) is shown disposed around the slide bar (61). Rollers (68), having sealed bearings, are spaced around the rectangular sleeve (67) on each face. Rigidly fixed to the sleeve (67) are connecting brackets (69) having an aperture (70) therein. The forward end of the third connecting member (65) has a clevis end (73) with mating apertures (72) therein. The apertures (70 and 72) are aligned to receive a connecting pin (74) to pivotally attach the sleeve (67) to the third connecting member (65). A passage (77) is located in the roller assembly (66). This passage (77) is positioned for alignment with a mating passage (77), at the forward end of the slide bar (61), or a mating passage (79), at the rearward end of the slide bar (61). The V-rake (10) can be locked in the transport position by inserting a pin (not shown) through the rearward aligned passages (77 and 79) and alternatively the V-rake (10) can be locked into the fully extended operative field position by inserting a pin through the forward aligned passages (77 and 78).

Figure 8:
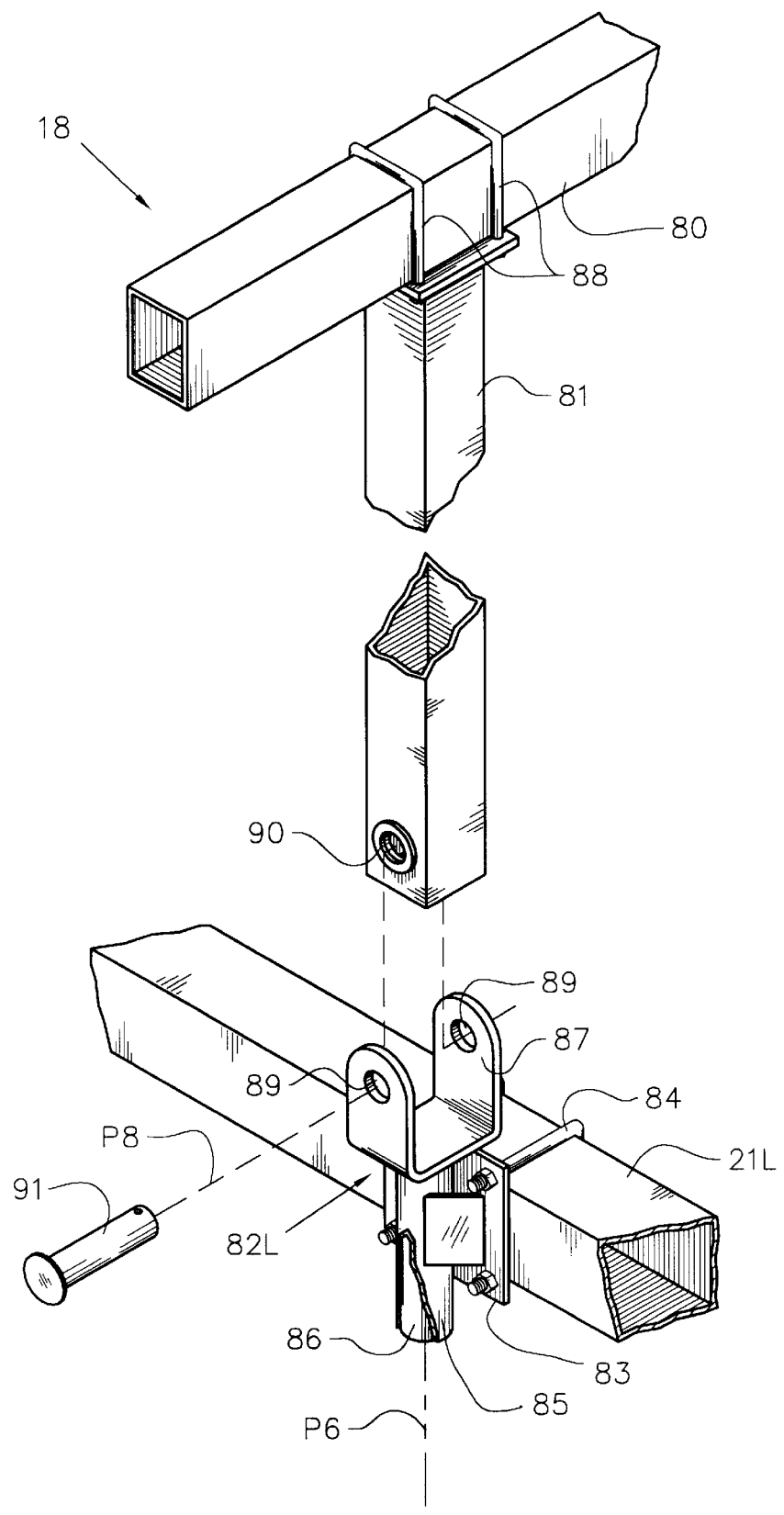
FIG. 8 shows an enlarged exploded perspective view of a portion of the rearward pivotal subframe.

Referring back to FIGS. 1 and 2, the rearward pivotal subframe (18) is shown in plan view pivotally attached to the rearward portion of the right and left handed rake assemblies (20R and 20L). An enlarged partial perspective view of the left side of the rearward pivotal connecting subframe (18) is shown in FIG. 8. The rearward pivotal subframe (18) is comprised of a horizontal cross beam (80) and vertical struts (81). The vertical struts (81) are rigidly secured at their upper ends to the horizontal cross beam (80) by a first set of U-bolt connectors (88). The lower ends of the vertical struts (81) are pivotally mounted to the main horizontal beams (21R and 21L) of the right and left hand rake assemblies (20R and 20L) through a dual pivot connecting assembly (82) that provides both a horizontal axis of rotation and a vertical axis of rotation for the rearward pivotal subframe (18).

The dual pivot connecting assembly (82) is comprised of a mounting plate (83) which is secured to the main horizontal frame members (21R and 21L) of the right or left hand rake assemblies (20R and 20L). A second set of U-bolt connectors (84) are shown securing the mounting plate (83) to the horizontal frame member (21L). The dual pivot connecting assembly (82) is further comprised of a vertical sleeve (85) fixed to the mounting plate (83) for receiving a rotatable shaft (86) rigidly fixed to a clevis-type bracket (87) thereby providing the first axis of rotation of the dual pivot connecting assembly (82). The clevis-type bracket (87) includes apertures (89) which align with reinforced apertures (90) in the lower end of the vertical strut (81). The apertures (89 and 90) receive a connecting pin (91) thereby connecting the vertical strut (81) to the clevis-type bracket (87) of the dual pivot assembly (82). This pinned connection enables the vertical strut (81) to freely rotate about the horizontal axis of the connecting pin (91) thus providing the second axis of rotation of the dual pivot connecting assembly (82).

It should be noted that the width of the windrow can be varied by loosening the first set of U-bolt connectors (88) and sliding the vertical struts (81) along the horizontal cross beam (80), thereby increasing or decreasing the distance between the rearward ends of the left and right wheel rake assemblies (20R and 20L). It should also be noted that the right and left hand wheel rake assemblies (20R and 20L) may be easily uncoupled so that each rake assembly (20R and 20L) may be used independently of each other. To uncouple the rakes (20R and 20L) the user may simply remove rearward pivotal subframe (18) by removing the U-bolts (84).

In operation, the hydraulic cylinders (76) are actuated to move the right and left handed rake assemblies (20R and 20L) from the folded transport position (shown in FIG. 1) to the operative field position (shown in FIG. 2). When the V-rake (10) is in the transport position, the pistons of the hydraulic cylinders (76) are extended as illustrated in phantom lines in FIG. 6. When unfolding the V-rake (10) to the operative field position, the pistons of the hydraulic cylinders (76) are withdrawn, causing the second and fourth connecting beams (63R and 63L) to rotate inwardly about the vertical pivot axes P2 and P3 (best viewed in FIG. 6) respectively, and the third connecting beam pivots about the vertical pivot axis P4. This inwardly rotating movement of the second and fourth connecting beams (63R and 63L) and third connecting beam (65) in turn causes the tow bar (60) to pivot about the vertical pivot axis P1. As the right and left wheel rake assemblies (20R and 20L) extend to the operative field position, the roller assembly (66) slides forwardly on the slide bar (61) to the position shown in FIG. 2. As the forward ends of the right and left hand rake assemblies (20R and 20L) are rotated outwardly by the forward pivotal subframe (17), the rearward ends of the right and left hand rake assemblies (20R and 20L) rotate inwardly about vertical pivot axes P5 (not shown) and P6 (see FIG. 8) of the right and left dual pivot connecting assemblies (82R and 82L). Note. FIG. 8 shows only the vertical pivot axes P6 of the left dual pivot connection assembly (82L). The vertical axes P5 of the right dual pivot connection assembly (82R) is simply a mirror image.

Figure 9:
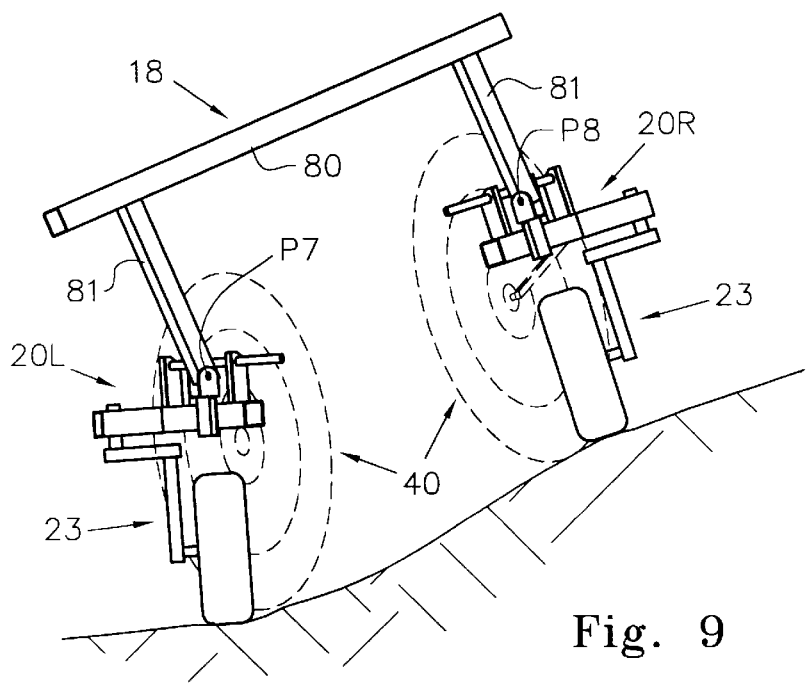
FIG. 9 is a rear view of the V-rake illustrating the ability of the left and right rake assemblies to articulate independently side-to-side when traversing uneven terrain.

FIG. 9 shows the articulating capabilities of the V-rake (10) of the present invention as it traverses uneven terrain. FIG. 9 is a rearview of the V-rake (10) showing the ability of the left and right rake assemblies (20R and 20L) to articulate vertically independently of each other about horizontal pivot axes P7 and P8. It should also be appreciated that the left and right rake assemblies (20R and 20L articulate independently of each other vertically front to rear). The advantage of this front-to-rear and side-to-side articulating action enables all of the wheel rakes (40) to remain in substantial contact at all times with the cut vegetation while traversing uneven terrain. The prior art V-rakes have heretofore used a central transport frame to which the left and right rake assemblies were attached. With each rake assembly fixed to a central transport frame, the wheel rakes often skipped over the cut vegetation. For example, when each rake assembly is fixed to a central transport frame, the terrain under the rake assemblies in their operative field position may be higher or lower than the terrain under the central transport frame. If the terrain is lower under the extended rake assembly than the terrain under the central transport frame, the rakes will skip over the cut vegetation.

Obviously many modifications and variations of the present invention are possible in light of the above teachings. It is therefore to be understood that, within the scope of the appended claims, the invention may be practiced otherwise than as specifically described.

I claim:

1. A V-rake for use in raking cut vegetation into windrows, comprising:
    (a) left hand and right hand, side discharge, wheel rake assemblies, each of said wheel rake assemblies comprising:
        (i) a main horizontal beam having a forward end and a rearward end;
        (ii) an intermediate subframe rigidly fixed to said main horizontal beam intermediate said forward and rearward ends and disposed inwardly thereof;
        (iii) at least two castor-type pivotal wheel assemblies operably supporting said main horizontal beam;
        (iv) a plurality of wheel rakes, operably pivotally connected to said main horizontal beam and spaced there along;
    (b) a forward pivotal subframe having a forward end and a rearward end, said forward end of said forward pivotal subframe connectable to a towing vehicle; said rearward end of said forward pivotal subframe operably pivotally connected to said intermediate subframes of said left and right wheel rake assemblies, whereby said forward pivotal subframe enables said left and right wheel rake assemblies to articulate independently side-to-side and independently from front to rear when traversing uneven terrain;
    (c) a dual pivoting rearward subframe, pivotally connected approximate said rearward ends of said main horizontal beams of said left and right wheel rake assemblies, whereby said rearward subframes enables said left and right wheel rake assemblies to articulate independently side-to-side and independently from front to rear when traversing uneven terrain; and
    (d) left and right hydraulic actuators operably pivotally connected to said forward pivotal subframe and said intermediate subframes of said right and left rake assemblies respectively whereby actuation of said right and left actuators moves said left and right rake assemblies from a transport position to a working position.

2. The V-rake of claim 1 wherein said forward pivotal subframe comprises:
    (a) a tow bar;
    (b) a slide bar fixed to said tow bar and extending obliquely rearwardly thereof;
    (c) a first connecting beam extending parallel to said slide bar and pivotally attached to said tow bar at a forward end and fixed to said slide bar at a rearward end;
    (d) a second connecting beam pivotally attached at a forward end to said first connecting beam and pivotally attached at a rearward end to said intermediate subframe of one of said rake assemblies;
    (e) a positioning assembly disposed about said slide bar and movable therealong;
    (f) a third connecting beam pivotally connected at a forward end to said movable assembly; and
    (g) a fourth connecting beam pivotally attached at a forward end to a rearward end of said third connecting beam and pivotally attached at a rearward end to said intermediate subframe of one other of said rake assemblies.

3. The V-rake of claim 2 wherein said positioning assembly of said forward pivotal subframe is a roller assembly.

4. The V-rake of claim 2 wherein said positioning assembly of said forward pivotal subframe is a sliding assembly.

5. The V-rake of claim 2 wherein said dual pivoting rearward subframe comprises:
    (a) a cross beam having left and right ends;
    (b) a left vertical strut connected at an upper end approximate said left end of said cross beam;
    (c) a right vertical strut connected at an upper end approximate said right end of said cross beam;
    (d) a left dual pivot connecting assembly having a horizontal axis of rotation and a vertical axis of rotation, said left connecting assembly being rigidly fixed to said left main horizontal beam of said left wheel rake assembly and receiving a lower end of said left vertical strut such that said left vertical strut can rotate about said horizontal and vertical axis of rotation; and
    (e) a right dual pivot connecting assembly having a horizontal axis of rotation and a vertical axis of rotation, said right connecting assembly being rigidly fixed to said right main horizontal beam of said right wheel rake assembly and receiving a lower end of said right vertical strut such that said right vertical strut can rotate about said horizontal and vertical axis of rotation.

6. The V-rake of claim 5 wherein said wheel rakes of said wheel rake assemblies are adjustable along a vertical arc from a transport position to an operative field position.

7. The V-rake of claim 6 wherein each of said wheel rakes of said wheel rake assemblies are spring biased thereby enabling each wheel rake to move independently in a vertical arc when encountering an obstruction.

8. The V-rake of claim 7 wherein at least one of said pivotal castor-type wheel assemblies includes a locking mechanism to lock the wheel in a transport position.

9. A V-rake for use in raking cut vegetation into windrows, comprising:
   (a) left hand and right hand, side discharge, wheel rake assemblies, each of said wheel rake assemblies comprising:
      (i) a main horizontal beam having a forward end and a rearward end;
      (ii) an intermediate subframe rigidly fixed to said main horizontal beam intermediate said forward and rearward ends and disposed inwardly thereof;
      (iii) three castor-type pivotal wheel assemblies, wherein two of said wheel assemblies are operably rigidly connected to said main horizontal beam and wherein another of said wheel assemblies is rigidly operably connected to said intermediate subframe;
      (iv) a plurality of wheel rakes, operably pivotally connected to said main horizontal beam and spaced there along;
   (b) a forward pivotal subframe, comprising:
      (i) a tow bar connectable to a towing vehicle;
      (ii) a slide bar fixed to said tow bar and extending obliquely rearwardly thereof;
      (iii) a first connecting beam extending parallel to said slide bar and pivotally attached to said tow bar at a forward end and fixed to said slide bar at a rearward end;
      (iv) a second connecting beam pivotally attached at a forward end to said first connecting beam and pivotally attached at a rearward end to said intermediate subframe of one of said rake assemblies;
      (v) a positioning assembly disposed about said slide bar and movable therealong;
      (vi) a third connecting beam pivotally connected at a forward end to said movable assembly;
      (vii) a fourth connecting beam pivotally attached at a forward end to a rearward end of said third connecting beam and pivotally attached at a rearward end to said intermediate subframe of one other of said rake assemblies;
   (c) a dual pivoting rearward subframe, comprising:
      (i) a cross beam having left and right ends;
      (ii) a left vertical strut connected at an upper end approximate said left end of said cross beam;
      (iii) a right vertical strut connected at an upper end approximate said right end of said cross beam;
      (iv) a left dual pivot connecting assembly having a horizontal axis of rotation and a vertical axis of rotation, said left connecting assembly being rigidly fixed to said left main horizontal beam of said left wheel rake assembly and receiving a lower end of said left vertical strut such that said left vertical strut can rotate about said horizontal and vertical axis of rotation;
      (v) a right dual pivot connecting assembly having a horizontal axis of rotation and a vertical axis of rotation, said right connecting assembly being rigidly fixed to said right main horizontal beam of said right wheel rake assembly and receiving a lower end of said right vertical strut such that said right vertical strut can rotate about said horizontal and vertical axis of rotation;
   (d) left and right hydraulic actuators, said left hydraulic actuator pivotally connected at one end to said left intermediate subframe of said left rake assembly and pivotally connected at another end to said second connecting beam of said forward pivotal subframe, said right hydraulic actuator pivotally connected at one end to said right intermediate subframe of said right rake assembly and pivotally connected at another end to said fourth connecting beam of said forward pivotal subframe;
   whereby actuation of said right and left actuators moves said left and right rake assemblies from a transport position to a working position and whereby said forward and rearward subframes enable said left and right wheel rake assemblies to articulate independently side-to-side and independently from front to rear when traversing uneven terrain.

10. The V-rake of claim 9 wherein said positioning assembly of said forward pivotal subframe is a roller assembly.

11. The V-rake of claim 9 wherein said positioning assembly of said forward pivotal subframe is a sliding assembly.

12. The V-rake of claim 9 wherein said wheel rakes of said wheel rake assemblies are adjustable along a vertical arc from a transport position to an operative field position.

13. The V-rake of claim 12 wherein each of said wheel rakes of said wheel rake assemblies are spring biased thereby enabling each wheel rake to move independently in a vertical arc when encountering an obstruction.

14. The V-rake of claim 13 wherein at least one of said pivotal castor-type wheel assemblies includes a locking mechanism to lock the wheel in a transport position.

15. A method of constructing a V-rake for use in raking cut vegetation into windrows, comprising:
   (a) providing left hand and right hand, side discharge, wheel rake assemblies, each of said wheel rake assemblies comprising:
      (i) a main horizontal beam having a forward end and a rearward end;
      (ii) an intermediate subframe rigidly fixed to said main horizontal beam intermediate said forward and rearward ends and disposed inwardly thereof;
      (iii) three castor-type pivotal wheel assemblies, wherein two of said wheel assemblies are operably rigidly connected to said main horizontal beam and wherein another of said wheel assemblies is rigidly operably connected to said intermediate subframe;
      (iv) a plurality of wheel rakes, operably pivotally connected to said main horizontal beam and spaced there along;
   (b) pivotally coupling said left hand and right hand wheel rakes assemblies for use as a single implement by utilizing a forward pivotal subframe and a dual pivoting rearward subframe, said forward pivotal subframe having a forward end and a rearward end, said forward end of said forward pivotal subframe connectable to a towing vehicle; said rearward end of said forward pivotal subframe operably pivotally connected to said intermediate subframes of said left and right wheel rake assemblies, said forward pivotal subframe being movable between a transport position and an operable working position; said dual pivoting rearward subframe being pivotally connected approximate said rearward ends of said main horizontal beams of said left and right wheel rake assemblies, whereby said forward and rearward subframes enable said left and right wheel rake assemblies to articulate independently side-to-side and independently from front to rear when traversing uneven terrain; and
   (c) providing left and right hydraulic actuators, said left actuator pivotally connected at one end to said left intermediate subframe of said left rake assembly and pivotally connected at another end to said forward pivotal subframe, said right actuator pivotally connected at one end to said right intermediate subframe of said right rake assembly and pivotally connected at another end to said forward pivotal subframe, whereby actuation of said right and left actuators moves said left and right rake assemblies from a transport position to a working position.

16. The method of claim 15 wherein said forward pivotal subframe comprises:

(a) a tow bar;

(b) a slide bar fixed to said tow bar and extending obliquely rearwardly thereof;

(c) a first connecting beam extending parallel to said slide bar and pivotally attached to said tow bar at a forward end and fixed to said slide bar at a rearward end;

(d) a second connecting beam pivotally attached at a forward end to said first connecting beam and pivotally attached at a rearward end to said intermediate subframe of one of said rake assemblies;

(e) a positioning assembly disposed about said slide bar and movable therealong;

(f) a third connecting beam pivotally connected at a forward end to said movable assembly; and (g) a fourth connecting beam pivotally attached at a forward end to a rearward end of said third connecting beam and pivotally attached at a rearward end to said intermediate subframe of one other of said rake assemblies.

17. The method of claim 16 wherein said positioning assembly of said forward pivotal subframe is a roller assembly.

18. The method of claim 16 wherein said positioning assembly of said forward pivotal subframe is a sliding assembly.

19. The method of claim 16 wherein said dual pivotal rearward subframe comprises:

(a) a cross beam having left and right ends;

(b) a left vertical strut connected at an upper end approximate said left end of said cross beam;

(c) a right vertical strut connected at an upper end approximate said right end of said cross beam;

(d) a left dual pivot connecting assembly having a horizontal axis of rotation and a vertical axis of rotation, said left connecting assembly being rigidly fixed to said left main horizontal beam of said left wheel rake assembly and receiving a lower end of said left vertical strut such that said left vertical strut can rotate about said horizontal and vertical axis of rotation; and (e) a right dual pivot connecting assembly having a horizontal axis of rotation and a vertical axis of rotation, said right connecting assembly being rigidly fixed to said right main horizontal beam of said right wheel rake assembly and receiving a lower end of said right vertical strut such that said right vertical strut can rotate about said horizontal and vertical axis of rotation.

20. The method of claim 19 wherein said wheel rakes of said wheel rake assemblies are adjustable along a vertical arc from a transport position to an operative field position.

21. The method of claim 20 wherein each of said wheel rakes of said wheel rake assemblies are spring biased thereby enabling each wheel rake to move independently in a vertical arc when encountering an obstruction.

22. The method of claim 21 wherein at least one of said pivotal castor-type wheel assemblies includes a locking mechanism to lock the wheel in a transport position.

* * * * *